(12) United States Patent
Stadtmiller

(10) Patent No.: US 6,848,903 B2
(45) Date of Patent: Feb. 1, 2005

(54) ORTHODONTIC APPLIANCE AND BAND ASSEMBLY

(75) Inventor: Allen J. Stadtmiller, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 92 days.

(21) Appl. No.: 10/301,297

(22) Filed: Nov. 21, 2002

(65) Prior Publication Data

US 2004/0101799 A1 May 27, 2004

(51) Int. Cl.$^7$ .................................................. A61C 7/00
(52) U.S. Cl. ........................................................ 433/23
(58) Field of Search ...................................... 433/23, 24

(56) References Cited

U.S. PATENT DOCUMENTS

| | | | |
|---|---|---|---|
| 2,062,395 A | | 12/1936 | Brusse et al. |
| 3,203,098 A | * | 8/1965 | Petraitis ....................... 433/23 |
| 3,521,355 A | | 7/1970 | Pearlman |
| 3,657,817 A | | 4/1972 | Kesling |
| 3,985,282 A | | 10/1976 | Miller et al. |
| 4,083,113 A | | 4/1978 | Miller et al. |
| 4,120,090 A | * | 10/1978 | Kesling ........................ 433/23 |
| 4,256,455 A | | 3/1981 | Förster |
| 4,842,513 A | | 6/1989 | Haarmann |
| 5,064,368 A | | 11/1991 | Lavin |
| 5,154,606 A | | 10/1992 | Wildman |
| 5,232,364 A | | 8/1993 | Rosen |
| 5,322,436 A | | 6/1994 | Horng et al. |
| 5,338,191 A | | 8/1994 | Hamula |
| 5,529,491 A | | 6/1996 | Hilgenfeldt et al. |
| 6,241,516 B1 | * | 6/2001 | Orikasa et al. ................ 433/17 |

* cited by examiner

Primary Examiner—Cary E. O'Connor
(74) Attorney, Agent, or Firm—James D. Christoff

(57) ABSTRACT

An orthodontic assembly includes a band having a reference mark that is placed at certain orientation. An appliance connected to the band is oriented relative to the mark so that a proper, precise orientation of the appliance with respect to the band can be achieved. Optionally, the assembly may be made with automated techniques using robotic equipment, a vision system and a programmable logic controller.

27 Claims, 3 Drawing Sheets

ORTHODONTIC APPLIANCE AND BAND ASSEMBLY

BACKGROUND OF THE INVENTION

1. Field of the Invention

This invention broadly relates to components used in the course of orthodontic therapy. More particularly, the present invention relates to an assembly of an orthodontic band and orthodontic appliance, as well as a method of making the same.

2. Description of the Related Art

Orthodontic treatment is a specialized area within the general field of dentistry. Orthodontic treatment involves movement of crooked or misaligned teeth to preferred locations and orientations along the dental arch. At the conclusion of treatment, the aesthetic appearance of the patient's oral structure is often greatly improved and in many instances the patient's occlusion, or function of the teeth during eating, is enhanced.

One type of orthodontic treatment involves the use of a set of components that are commonly known collectively as "braces". These components include a set of small slotted devices known as brackets that are secured to the patient's anterior, cuspid and bicuspid teeth. An archwire is held in the slots of the brackets and functions as a track to guide movement of the teeth to orthodontically correct positions. The teeth are often moved by bends or twists placed in the archwire or by elastic members connected to one or more of the brackets.

Oftentimes, small devices known as buccal tubes are secured to the molar teeth. The buccal tubes have elongated enclosed passageways that receive ends of the archwires. Some buccal tubes have "convertible" passageways that can be opened along one side in order to convert the appliance into a slotted bracket when desired.

In past years, it was common practice to weld each buccal tube and bracket to a corresponding orthodontic band. The orthodontic bands were selected to match the contour and circumferential dimensions of the tooth so that a close, non-loosening fit between the band and the tooth could be achieved. In more recent years, however, adhesives have been developed that have sufficient strength to affix brackets and buccal tubes directly to the surfaces of the tooth without the need for a band.

However, buccal tubes are often subjected to relatively large forces from occluding teeth as well as forces exerted by the archwire. In addition, molar teeth have relatively large roots and are sometimes used as an anchoring location for resisting forces imposed by orthodontic components that are connected to other teeth in the oral cavity. As a result, many practitioners prefer to continue to use buccal tubes that are connected to an orthodontic band so that a stable support platform for the buccal tube is provided.

Welded bracket and band assemblies are also still used in certain instances with anterior, cuspid and bicuspid teeth. For example, in some cases a relatively strong connection to a tooth is desired and the use of a band ensures that the bracket will remain securely coupled to the associated tooth. In other instances, the patient may have a weak or fractured tooth or a tooth restoration that may preclude the bonding of a bracket directly to a tooth with sufficient strength to safely resist the expected forces that may be encountered during the course of treatment.

Other orthodontic appliances may also be connected to bands instead of brackets or buccal tubes. Examples of such other appliances include cleats, buttons, hooks, lingual sheaths and eyelets. The appliances may be mounted either on the buccolabial side of the band (i.e., the side facing the patient's cheeks or lips) or on the lingual side of the band (i.e., the side facing the tongue of the patient).

Typically, orthodontic bands and the appliances that are connected to bands are made of a metallic material such as stainless steel. These assemblies are often connected together by a brazing or welding process. An improved process for welding appliances to bands is described in applicant's U.S. Pat. No. 5,529,491.

The shape of orthodontic bands is generally considered complex. Many orthodontic bands are provided with rounded protrusions that extend inwardly toward the middle of the band. These protrusions are adapted to fit within small recesses of a patient's tooth, such as the concave regions between adjacent cusps of a patient's molar tooth. Protrusions help to mechanically interconnect the band to the tooth and reduce the likelihood that the band will shift or rock during the course of treatment. In addition, the use of protrusions that match the shape of recesses in a patient's tooth can avoid undue gaps between the band and underlying areas of the tooth that might otherwise trap food and promote tooth decay.

Moreover, one or both edges of the band may extend along an undulating path that does not lie in a flat reference plane. For example, the gingival perimeter (i.e., the perimeter facing the patient's gingiva or gums) may extend outwardly in a gingival direction along a curved path in areas next to the buccolabial side of the patient's tooth and the lingual side of the tooth. In those areas, the gingiva is normally located a relatively large distance from the outer tip of the tooth. However, in areas adjacent the mesial side of the tooth (i.e., the side of the tooth facing the middle of the patient's dental arch) and the distal side of the tooth (i.e., the side of the tooth facing away from the middle of the patient's dental arch) the perimeter of the band may curve in an occlusal direction. In those areas, the gingiva is typically located closer to the outer tip of the tooth. Such construction helps to avoid contact of the band with the patient's gingival and yet provides good resistance to lateral movement or rocking during use.

Similarly, the occlusal edge of the band may curve in an occlusal or gingival direction in different regions along its perimeter. For example, the occlusal edge may curve in a gingival direction in order to avoid extending past the tooth in an occlusal direction, particularly in areas between the cusps of molar teeth as described above.

The position of the appliance on the band is an important consideration during treatment. For example, if the band is not placed in a correct location along a mesial-distal reference axis, the archwire may cause the tooth to be rotated about its long axis to an undesirable orientation. Similarly, if the appliance is not placed on the band in a correct location with respect to an occlusal-gingival reference axis, the archwire may cause the tooth to be moved to an unsatisfactory location in an occlusal or gingival direction. For these reasons, orthodontic practitioners are often careful to specify the exact position of the appliance on the band for each patient, depending on the treatment at hand.

However, it has been a cumbersome procedure in the past for manufacturers to ensure that appliances were positioned on the bands at precise, correct locations. In some cases, the band was placed in a first jig having a shape that matched the shape of the band, including protrusions formed in the band. A second jig was also provided to hold the appliance and orient the appliance to the desired location on the band.

Unfortunately, the protrusions described above do not provide a precise, consistent means of orienting the band to the jigs. The protrusions are typically smoothly curved and the center of the curve may be difficult to ascertain. As a consequence, the accuracy of placement of the appliance on the band is impaired.

Consequently, in the past it has been common practice to visually inspect each band at close range by an inspector in the manufacturer's facility using a toolmaker's eye scope or video camera. Visual inspection is used initially to ensure proper orientation of the appliance to the band before the appliance and the band are welded together. The visual inspection can also be used subsequent to the welding process to ensure that the appliance and band are correctly oriented relative to each other after assembly.

As can be appreciated, manual inspection by eye is somewhat time-consuming and can significantly contribute to the overall costs of the assembly. Moreover, such a procedure is not foolproof in that operator inattention or error may result in an incorrectly positioned assembly. Unfortunately, it is difficult for the orthodontic practitioner to detect whether or not the band and the appliance are correctly assembled. If an improperly assembled assembly is used, the ultimate position or orientation of the tooth or teeth at the conclusion of orthodontic treatment may not be satisfactory and an additional treatment period may be needed.

Clearly, there is a need in the art for an improved means of manufacturing an orthodontic appliance and band assembly. Preferably, such a method would be useful both in the manufacturing plant as well as in the laboratories of orthodontic practitioners who prefer to weld appliances to bands in their offices.

SUMMARY OF THE INVENTION

The present invention is directed to an orthodontic appliance and band assembly, wherein the band has a mark placed at a certain location. The mark provides a convenient reference for orienting the orthodontic appliance to the band at a time during manufacture when it is desired to connect the appliance to the band. The mark also provides a convenient accuracy check so that the manufacturer as well as the practitioner can confirm that the appliance is in its proper placement relative to the band after assembly.

In more detail, the present invention in one aspect relates to a method of connecting an orthodontic appliance to a band. The method includes the acts of providing a band preform having a generally cylindrical configuration and stretching the preform as may be needed to make a band having a configuration matching a portion of the configuration of the tooth. The method also includes the acts of providing a mark on the band at a certain location after the band preform has been stretched and placing the orthodontic appliance on the band at a certain orientation relative to the mark by using the mark as a guide. The method further includes the act of fixing the orthodontic appliance in place at the certain orientation on the band.

Another aspect of the invention is directed toward an orthodontic assembly. The assembly comprises a band adapted to encircle a tooth. The band has an external buccolabial surface, an external lingual surface, an external mesial surface and an external distal surface. The band includes at least one mark located on the buccolabial surface. The assembly also includes an orthodontic appliance that is affixed to the buccolabial surface of the band. The appliance is located in a certain, predefined orientation relative to the mark.

The present invention is particularly useful for automated manufacturing techniques. The reference mark can be detected by a vision system and the orientation of the appliance relative to the band can be carried out by robotic devices. Alternatively, the reference mark can be used by either the manufacturer or by the practitioner in instances where manual orientation of the appliance relative to the band is desired.

These and additional aspects of the invention will be described in more detail below and are illustrated in the accompanying drawings.

DETAILED DESCRIPTION OF THE PREFERRED EMBODIMENTS

Figure 1:
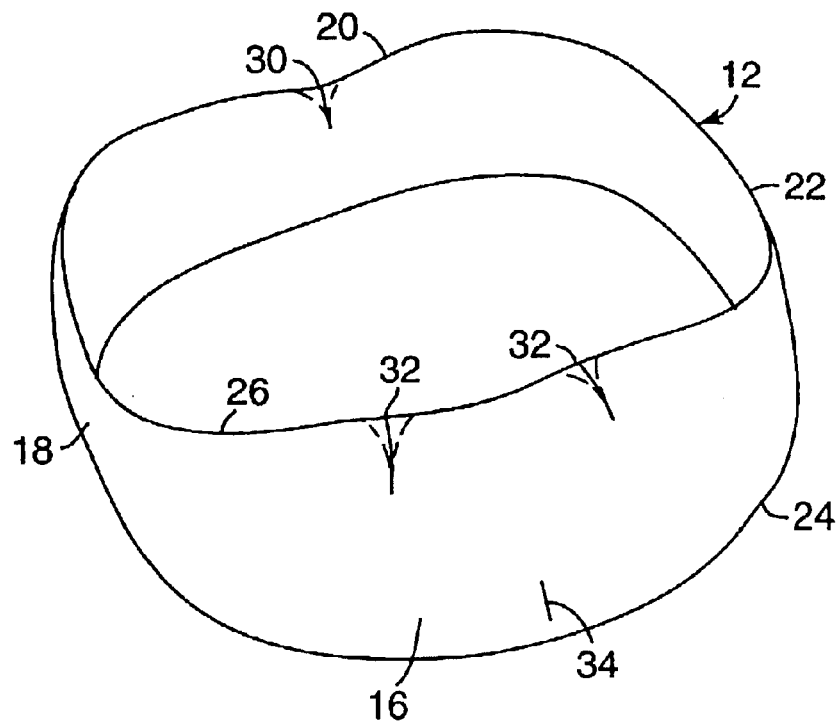
FIG. 1 is a perspective view of an orthodontic band of an appliance and band assembly that is constructed in accordance with one embodiment of the present invention.
Figure 2:
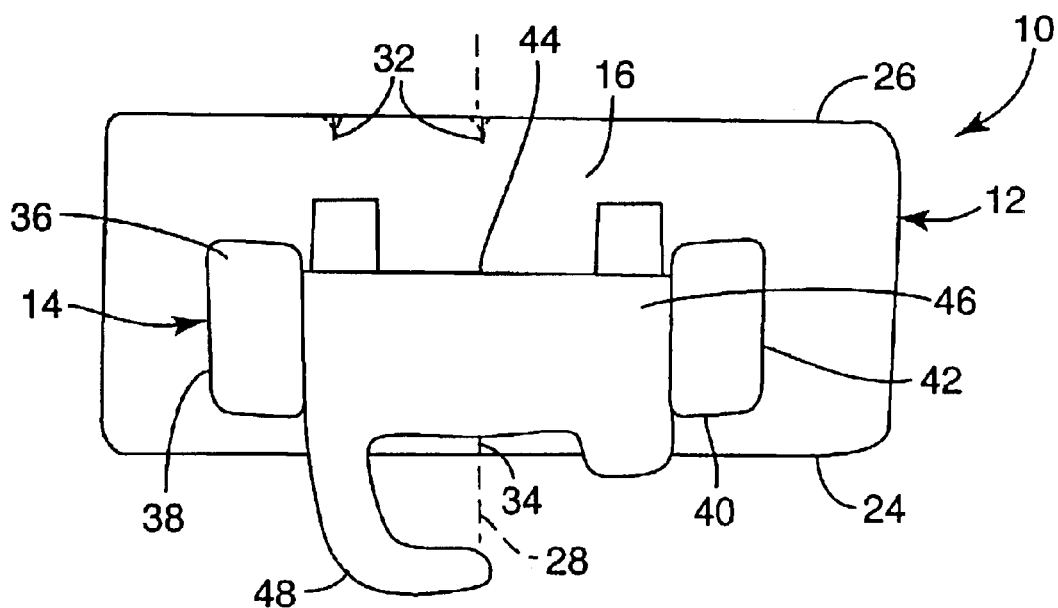
FIG. 2 is a front elevational view of the band shown in FIG. 1 along with an orthodontic appliance that has been connected to the band.

An orthodontic appliance and band assembly according to one embodiment of the present invention is shown in FIG. 2 and is broadly designated by the numeral 10. The assembly 10 includes an orthodontic band 12 and an orthodontic appliance 14 that is fixed to the band 12. The band 12 is shown alone in FIG. 1.

As depicted in FIG. 1, the band 12 includes an external buccolabial surface 16, an external mesial surface 18, an external lingual surface 20 and an external distal surface 22. All of the surfaces 16–22 are integrally connected to each other by curved corner portions. The band 12 also includes a gingival edge or perimeter 24 that faces the patient's gingiva when the band 12 mounted on a tooth, and an occlusal edge or perimeter 26 that faces the occlusal tip of the tooth. The band 12 has an overall tubular configuration with a central reference axis 28 that is shown only in FIG. 2.

Preferably, the gingival perimeter 24 presents an undulating or wavy-appearing edge that does not lie in a flat reference plane parallel to the central axis 28. The gingival perimeter 24 preferably matches and follows along the interface or margin between the patient's gingiva and the tooth upon which the band 12 is mounted.

In particular, the gingival perimeter 24 is preferably curved away from the occlusal perimeter 26 in directions parallel to the central axis 28 in regions along the buccolabial surface 16 and the lingual surface 20. The gingival perimeter 24 is curved toward the occlusal perimeter 24 in directions along the central axis 28 in regions along the mesial surface 18 and the distal surface 22. Such construction increases the surface area of the band 12 that is in contact with the tooth to help ensure that the band 12 does not unduly rock on the tooth and instead is securely and non-movably connected to the same. Such construction also helps ensure that the gingival perimeter 24 does not contact the patient's gingiva once the band 12 is in place.

The occlusal perimeter 26 as shown in the drawings generally lies in a flat plane that is substantially perpendicular to the central axis 28. As an alternative, however, the occlusal perimeter 26 may also extend along a wavy path that curves in opposite directions parallel to the central axis 28. In the latter alternative, the curved path-preferably matches the shape of the occlusal tip portion of the patient's tooth once the band 12 is in place on the tooth.

Optionally, the band 12 is provided with protrusions or notches that are adapted to nest within mating recesses or concavities of the patient's tooth structure. In the embodiment shown in the drawings, the band 12 includes a single lingual protrusion 30 and two buccolabial protrusions 32. The protrusions 30, 32 are shaped in this instance to fit within recesses located between cusps of a lower first molar tooth. When the band 12 is constructed to fit other molar teeth, the band 12 preferably has only a single buccolabial protrusion and a single lingual protrusion. The band may lack protrusions when constructed to fit teeth other than molar teeth, since in those instances the recesses in the tooth do not exist or are not prominent.

The band 12 also includes a reference mark 34 as illustrated in FIG. 1. In this embodiment, the mark 34 is elongated and extends in a direction substantially parallel to the central axis 28. Additionally, the mark 34 is located at the approximate center of the buccolabial surface 16 in directions perpendicular to the axis 28 (i.e., in mesial and distal directions), but is located closer to the gingival perimeter 24 than the occlusal perimeter 26.

The orthodontic appliance 14 that is shown in FIG. 2 includes a base 36 having a surface adapted for connection to the buccolabial surface 16 of the band 12. Optionally, the base 36 is concave in order to matingly fit against a convex region of the buccolabial surface 16. The concave configuration of the base 36 may be provided in reference planes perpendicular to the axis 28 or in reference planes parallel to the axis 28, or both.

The base 36 in this embodiment includes a rectangular perimeter with a mesial edge 38, a gingival edge 40, a distal edge 42 and an occlusal edge 44. The appliance 14 also includes a body 46 that extends outwardly from the base 36. The body 46 includes a passageway (not shown) for receiving an archwire, and a hook 48 is integrally connected to the body 46.

The appliance 14 illustrated in FIG. 2 is known as a buccal tube and is only one example of a variety of appliances that may be utilized with the assembly of the present invention. Other examples of orthodontic appliances for use in the assembly 10 include brackets, cleats, buttons, hooks, eyelets and other devices as may be deemed desirable by the practitioner. Moreover, the base of the appliance need not be rectangular; for example, the appliance may have a perimeter in the shape of a square, circle, oval, trapezoid or parallelogram or may have a shape resembling the adjacent exposed surface of the tooth.

The appliance 14 is positioned on the band 12 such that the appliance 14 is located in a certain, predefined orientation relative to the mark 34. Consequently, the mark serves to identify a precise reference location for the appliance 14 during the time that the band 12 and the appliance 14 are assembled together. Moreover, the mark 34 serves to verify that the appliance 14 is in a correct position on the band 12 after such time as the appliance 14 and the band 12 have been fixed together.

For example, and with respect to the embodiment shown in FIG. 2, the manufacturer may elect to pre-determine a desired distance between the mark 34 and the mesial edge 38 of the appliance base 36. Consequently, once the appliance 14 is brought into proximity with the buccolabial surface 16, the actual, initial distance between the mesial edge 38 and the mark 34 can be determined. The relative position between the appliance 14 and the band 12 is then adjusted as needed in order to place the mesial edge 38 at the precise, pre-determined desired distance relative to the mark 34.

A variety of alternative positioning techniques are also possible. For example, the distal edge 42 of the base 36 may be used instead of the mesial edge 38. Other features of the appliance 14, such as the mesial side or distal side of the body 46, may also be used.

Optionally, the gingival perimeter 24 or the occlusal perimeter 26 of the band 12 may be used in combination with the mark 34 to establish the proper orientation of the appliance 14 on the band 12. Specifically, the occlusal perimeter 26 and/or the gingival perimeter 24 may be used to establish the proper orientation of the appliance in directions parallel to the central reference axis of the band. Preferably, the occlusal perimeter 26 lies in a flat reference plane perpendicular to the axis 28 and is used with the mark 34 to orient the appliance 14. In this example, the mark 34. is only used to establish the proper orientation of the appliance in a mesial-distal direction, or in directions perpendicular to the central reference axis of the band.

Figure 3:
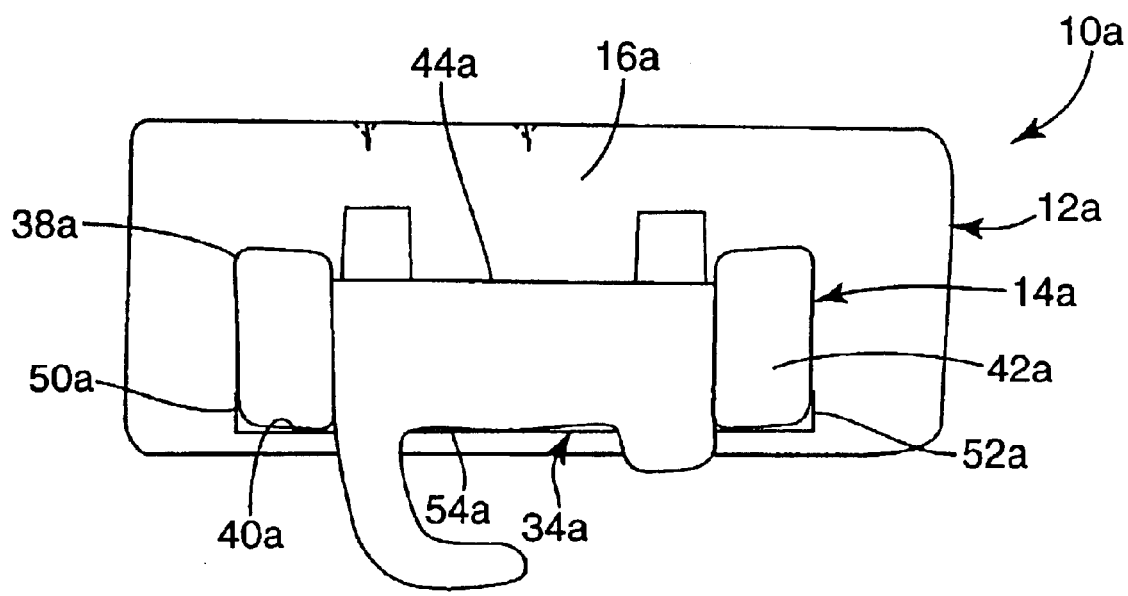
FIG. 3 is a view somewhat similar to FIG. 2 except that the band is provided with a reference mark that is somewhat different than the reference mark of the band shown in FIGS. 1 and 2.

FIG. 3 illustrates an alternative embodiment of the invention. In FIG. 3, an assembly 10*a* includes a band 12*a* and an appliance 14*a*. The band 12*a* has a buccolabial surface 16*a* with a mark 34*a*. The mark 34*a* is placed in a certain, pre-defined orientation relative to the appliance 14*a*.

The mark 34*a* includes a mesial section 50*a* as well as a distal section 52*a*. In addition, a central section 54*a* extends between the mesial section 50*a* and the distal section 52*a*. The central section 54*a* extends in a plane substantially perpendicular to a central reference axis of the band. 12*a*, while the mesial and distal sections 50*a*, 52*a* extend in a direction substantially parallel to the central reference axis. The central reference axis is not illustrated in the drawings, but is identical to the central reference axis 28 described above.

In the embodiment shown in FIG. 3, the mesial section 50*a* is located adjacent a mesial edge 38*a* of the appliance 14*a* and the distal section 52*a* is located adjacent a distal edge 42*a* of the appliance 14*a*. Optionally, a slight space exists between the mesial section 50*a* and the mesial edge 38*a*, and between the distal section 52*a* and the distal edge 42*a*, to ensure that both the sections 50*a*, 52*a* are visible after the appliance 14*a* is fixed in place on the band 12*a*. Similarly, the central section 54*a* is located adjacent a gingival edge 40*a* of the appliance 14*a*. Alternatively, the central section 54*a* may be located adjacent an occlusal edge 44*a* of the appliance 14*a*.

Other features of the band 12*a* are identical to the band 12, and other features of the appliance 14*a* are identical to the appliance 14. Consequently, a detailed description of those features need not be repeated.

A number of alternative marks, in substitution for or in addition to the mark 34 or the mark 34a, are possible. For example, the mark may extend along the entire perimeter of the base of the appliance or only along one or more corners of the appliance. The mark may include sections that are spaced apart from each other, such as mesial and distal sections that extend parallel to each other but lack an interconnecting central section as shown in FIG. 3. As other alternatives, the mark may consist of a series of dots or dashes instead of the continuous elongated sections depicted in the drawings.

Optionally, the mark may be obscured or partially obscured by the appliance after the appliance is secured to the band. For example, the orientation and overall size of the mark may be selected so that the base of the appliance completely covers the mark after the appliance and the band are assembled together. However, as presently preferred the mark is at least partially visible after assembly, so that the manufacturer and/or the practitioner can readily check to ensure that the appliance is placed in a proper orientation on the band.

The mark, such as the marks 34 and 34a, may be made by indenting the buccolabial surface of the band, preferably using a tool that forms a sharp, precise groove. Alternatively, the mark may be made by using a laser such as the one described in U.S. Pat. No. 5,322,436. As further alternatives, the mark may be made by machine tools (such as a mill or scribe) or by a marking tool that leaves a deposit of ink or other composition on the surface of the band. A chemical etchant may also be employed.

The following paragraphs set out the method of manufacturing the assembly 10. Initially, an orthodontic band preform made of a metallic material (such as 305 stainless steel) is provided. The preform has a shape somewhat similar to a tubular cylinder. Preferably, the perform has a gingival perimeter with a wavy shape (as described above). The band preform is tumbled to polish its stainless steel external surface. In addition, the preform is heat treated in an annealing process.

Figure 4:
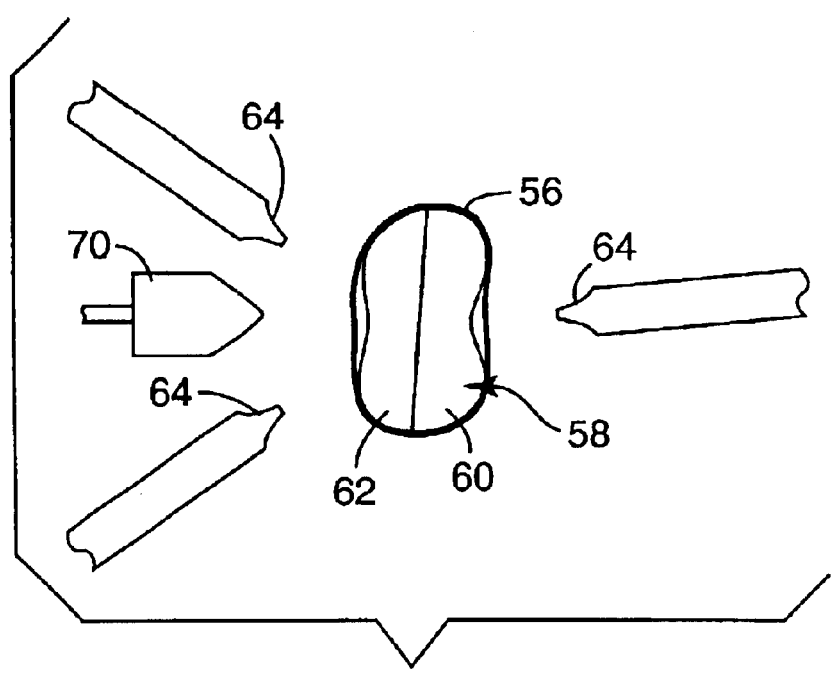
FIG. 4 is a schematic plan view of tooling for making the band of the present invention, wherein a band preform has been placed over a two-piece mandrel.

The band preform is then placed over a mandrel as shown in FIG. 4. In FIG. 4, the preform is designated by the numeral 56 and the mandrel by the numeral 58. The mandrel 58 includes a first section 60 and a second section 62. The sections 60, 62 are movable toward and away from each other when desired. As an alternative to the mandrel 58, an expander may be used.

Preferably, the preform 56 includes a reference mark (not shown) to facilitate relative rotative alignment of the preform relative to the mandrel 58. For example, the preform 56 may have a small protrusion that is located in a certain rotative position relative to the undulations of the gingival perimeter. In this manner the undulations can be properly oriented relative to the first and second sections 60, 62.

Figure 5:
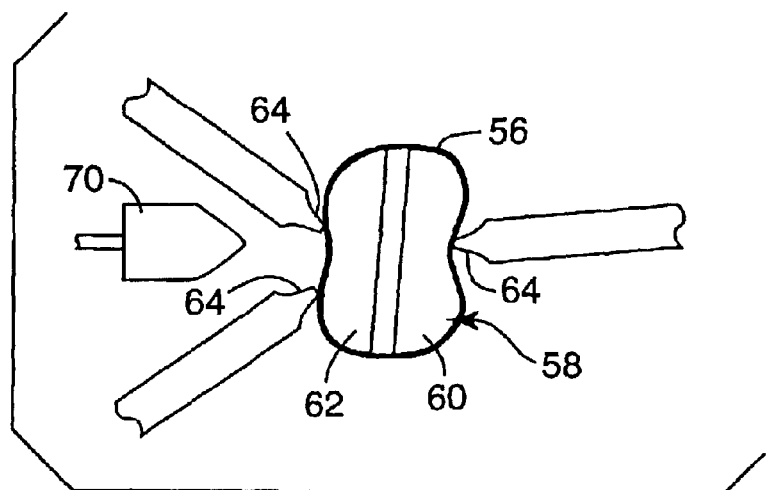
FIG. 5 is a view somewhat similar to FIG. 4 except that the two pieces of the mandrel have been moved apart in order to stretch the band preform and three forming tools have been advanced toward the mandrel to contact the preform and shape the preform to match the configuration of a tooth.

Next, the mandrel sections 60, 62 are moved away from each other and to the orientations shown in FIG. 5. As the sections 60, 62 move apart, the preform 56 is stretched past its yield point such that the inner surface of the preform 56 substantially assumes the external shape of the mandrel 58. As the mandrel 58 expands, the protrusion mentioned above that is used as a reference mark for placing the preform 56 on the mandrel 58 is stretched out and essentially disappears.

Subsequently, and as illustrated in FIG. 5, three "notchers" or forming tools 64 are advanced toward the stretched preform 56 for contact with the latter. The paths of the three forming tools 64 are aligned with three recesses provided along the side of the mandrel 58. The tip of each forming tool 64 is made of hardened steel and has a bulbous shape that matches the corresponding recess in the mandrel 58.

The forming tools 64 press against the preform 56 with sufficient force to locally stretch the preform 56 past the yield point of the stainless steel material and form three protrusions. One protrusion is the lingual protrusion 30 described above, and the other two protrusions are the buccolabial protrusions 32 described above.

Figure 6:
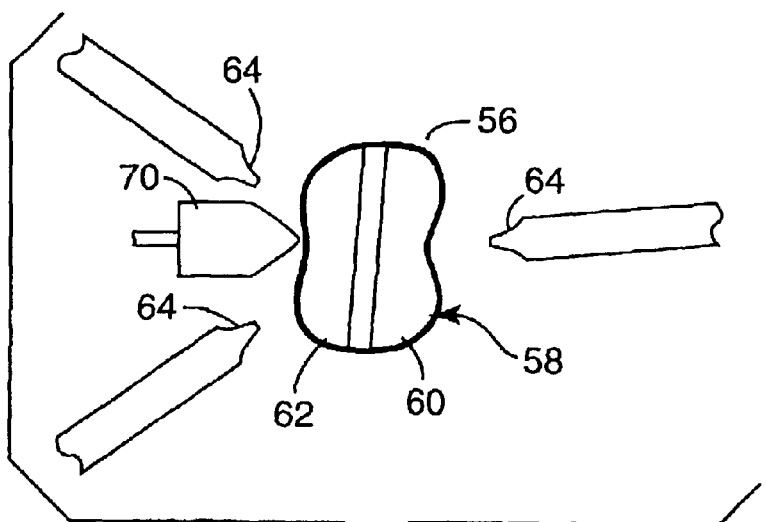
FIG. 6 is a schematic front elevational view of the mandrel tooling, band and forming tools depicted in FIG. 5.

FIG. 6 is a schematic, reduced side elevational view showing exemplary devices for moving the forming tools 64. In this illustration, pneumatic piston and cylinder assemblies 66 (only two are illustrated in FIG. 6) each include a piston that is coupled to a drive rod 68. Each drive rod 68 is connected to one of the forming tools 64. Optionally, all three of the piston and cylinder assemblies 66 can be activated simultaneously. Although not shown in the drawings, a pair of pneumatic piston and cylinder assemblies are also provided for movement of the mandrel sections 60, 62 when desired.

Figure 7:
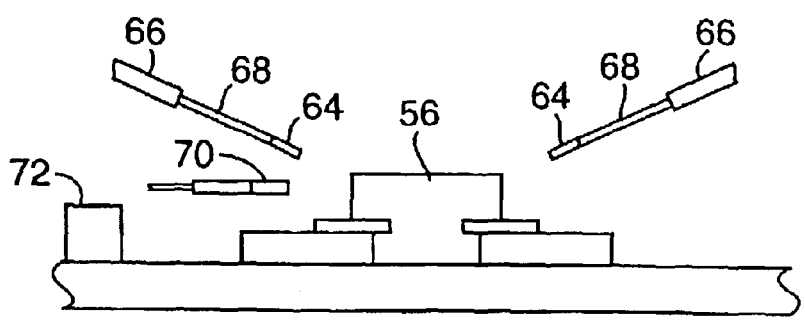
FIG. 7 is a view somewhat similar to FIG. 5 except that a marking tool has been advanced toward the mandrel in order to contact the band and make a reference mark.

Next, and as depicted in FIG. 7, a forming tool 70 is advanced toward the preform 56 which, at this point, has assumed the configuration of the band 12. The forming tool 70 contacts the band 12 with sufficient force to locally stretch the stainless steel material past its yield point and indent the same in order to form the mark 34. Preferably, and in contrast to the forming tools 64, the forming tool 70 has a sharp elongated tip so that a distinct, precise elongated mark 34 is provided. The tip is preferably made of hardened steel, although other materials are also possible.

Optionally, the forming tool 70 contacts the band 12 while the forming tools 64 remain in contact with the band 12. Alternatively, however, the forming tools 64 may be retracted before such time as the forming tool 70 is advanced. The latter alternative is particularly useful in instances where clearance between the forming tools 64 and the forming tool 70 is limited and might otherwise present a problem.

Next, the forming tool 70 (and the forming tools 64, if still in contact with the band 12) is retracted. The mandrel sections 60, 62 are then moved toward each other to enable the band 12 to be removed from the mandrel 58.

Preferably, the band 12 is then further tumbled to polish its external surfaces. Optionally, the inner surface of the band 12 may be mechanically or chemically treated to enhance the bond between the band 12 and the tooth upon which it is mounted. For example, the inner surface of the band 12 may be etched with a chemical agent or roughened with a sand blasting apparatus. Finally, the band 12 is cleaned with a chemical cleaning agent and the surface of the band 12 is passivated as needed.

Advantageously, some or all of the steps set out above may be carried out by use of a programmable logic controller, a vision system and robotic equipment. For example, robotic equipment may place the preform 56 on the mandrel 58. The vision system then detects the preliminary reference mark as mentioned above and the logic controller activates the robotic equipment as needed to properly orient the preform 56 relative to the mandrel 58.

Next, the logic controller (represented by the box 72 in FIG. 6) sequentially activates the pneumatic piston and cylinder assemblies for movement of the mandrel sections 60, 62, the piston and cylinder assemblies 66 for movement of the forming tools 64, and the piston and cylinder assembly for movement of the forming tool 70. After the protrusions 30, 32 are made, the piston and cylinder assemblies are retracted to move the tools 64 away from the band 12. After the mark 34 is made, the logic controller retracts the forming tool 70. The logic controller 72 then retracts the piston and cylinder assemblies connected to the first and second mandrel sections 60, 62 and activates the robotic equipment for removing the band 12 from the mandrel 58.

The band 12 is then placed in a holder. Next, robotic equipment places the appliance 14 adjacent the buccolabial surface 16 of the band 12. The vision system detects the orientation of the appliance 14 and the reference mark 34. The logic controller 72 then activates the robotic equipment as needed in order to properly orient the appliance 14 relative to the band 12.

A welder is subsequently activated by the logic controller 72 in order to securely fix the appliance 14 to the band 12 by one or more welds. The welds may be spot welds or laser welds. Alternatively, the welds may be tack welds and the appliance 14 is subsequently brazed to the band 12 in a furnace.

Optionally, the method of welding described in U.S. Pat. No. 5,529,491 may be employed for connecting the band 12 to the appliance 14. The entire disclosure of U.S. Pat. No. 5,529,491 is hereby incorporated by reference herein. The welding method described in that reference provides an aesthetic weld with deformations that are difficult to see by the naked eye.

The vision system described above can then be used to check the orientation of the appliance 14 relative to the band 12 to ensure that a proper precise orientation has been achieved. If the resultant orientation is not within specification, the logic controller 72 activates the robotic equipment to remove the welded assembly and place it in a reject container. If the orientation of the appliance 14 and the band 12 is within specification, the robotic equipment instead places the welded assembly into another container for additional processing steps (such as the tumbling and cleaning operations described above).

The embodiments described above represent only a few examples of the present invention, and many variations are possible. For example, the appliance may be a lingual appliance and connected to the lingual surface of the band. In that instance, the mark is preferably placed on the lingual surface of the band. Additionally, the band may be shaped to match the configuration of teeth other than the molar teeth.

A number of other alternatives are also possible. As such, the invention should not be deemed limited to the description set out in detail above, but instead only by a fair scope of the claims that follow along with their equivalents.

What is claimed is:

1. A method of connecting an orthodontic appliance to a band comprising:
   providing a band preform having a generally cylindrical configuration;
   stretching the preform as may be needed to make a band having a configuration matching a portion of the configuration of a tooth;
   providing a mark on the band at a certain location after the band has been stretched;
   placing the orthodontic appliance on the band at a certain orientation relative to the mark; and
   fixing the orthodontic appliance in place at the certain orientation on the band.

2. A method of connecting an orthodontic appliance to a band according to claim 1 wherein the act of placing the orthodontic appliance on the band is carried out such that the mark is visible after placement.

3. A method of connecting an orthodontic appliance to a band according to claim 1 wherein the act of placing the orthodontic appliance on the band is carried out such that the mark is obscured after placement.

4. A method of connecting an orthodontic appliance to a band according to claim 1 wherein the act of providing a mark on the band is carried out by indenting the band.

5. A method of connecting an orthodontic appliance to a band according to claim 4 wherein the act of providing a mark on the band is carried out by making a series of one or more marks that are aligned with a substantially straight reference axis.

6. A method of connecting an orthodontic appliance to a band according to claim 4 wherein the act of providing a mark on the band is carried out by supporting an inner surface of the band while the band is indented.

7. A method of connecting an orthodontic appliance to a band according to claim 1 wherein the act of providing a mark on the band is carried out by placing the mark in a middle region of the band with respect to a mesial-distal reference axis.

8. A method of connecting an orthodontic appliance to a band according to claim 1 and including the act of forming the band to provide protrusions to match recesses of the tooth.

9. A method of connecting an orthodontic appliance to a band according to claim 8 wherein the act of providing a mark on the band is carried out subsequent to the act of forming the band to provide protrusions.

10. A method of connecting an orthodontic appliance to a band according to claim 1 wherein the orthodontic appliance is a buccal tube.

11. A method of connecting an orthodontic appliance to a band according to claim 1 wherein the orthodontic appliance is a molar appliance.

12. A method of connecting an orthodontic appliance to a band according to claim 1 and including the act of detecting the location of the mark on the band with a vision system.

13. A method of connecting an orthodontic appliance to a band according to claim 12 and including the act of detecting the orientation of the band.

14. A method of connecting an orthodontic appliance to a band according to claim 13 wherein the act of detecting the orientation of the band is carried out by the vision system.

15. A method of connecting an orthodontic appliance to a band according to claim 1 wherein the act of stretching the band is carried out with a pair of mandrel sections that move away from each other.

16. A method of connecting an orthodontic appliance to a band according to claim 15 wherein the act of providing the mark on the band is carried out while the mandrel sections are moved apart and stretching the band.

17. A method of connecting an orthodontic appliance to a band according to claim 15 and including the act of moving the forming tools by a pneumatic piston and cylinder assembly.

18. A method of connecting an orthodontic appliance to a band according to claim 1 wherein the act of providing a mark on the band is carried out at least in part by making an elongated mark that extends in a direction generally parallel to a central axis of the band.

19. A method of connecting an orthodontic appliance to a band according to claim 1 wherein the mark comprises one or more dots or dashes.

20. An orthodontic assembly comprising:

a band adapted to encircle a tooth, wherein the band has an external buccolabial surface, an external lingual surface, an external mesial surface and an external distal surface, and wherein the band includes at least one mark located on the buccolabial surface; and an orthodontic appliance affixed to the buccolabial surface of the band and located in a certain, predefined orientation relative to the mark, wherein the mark includes at least one section that is spaced from the appliance such that at least a portion of the mark on the buccolabial surface is visible.

21. An orthodontic assembly according to claim 20 wherein the mark comprises a groove.

22. An orthodontic assembly according to claim 20 wherein the mark is a laser-engraved mark.

23. An orthodontic assembly according to claim 20 wherein the mark is a machined mark.

24. An orthodontic assembly according to claim 20 wherein the appliance is a buccal tube.

25. An orthodontic assembly according to claim 20 wherein the appliance is molar appliance.

26. An orthodontic assembly according to claim 20 wherein the mark comprises a series of one or more dashes or dots.

27. An orthodontic assembly according to claim 20 wherein the mark has a longitudinal axis.

* * * * *